United States Patent
Bassuk et al.

(10) Patent No.: US 6,726,639 B2
(45) Date of Patent: Apr. 27, 2004

(54) MEDICAL CUIRASS FOR CARDIO-PULMONARY RESUSCITATION

(76) Inventors: Jorge I. Bassuk, 1638 S. Bayshore Ct., Coconut Grove, FL (US) 33133; Jose A. Adams, 780 Lake Rd., Miami, FL (US) 33140

( * ) Notice: Subject to any disclaimer, the term of this patent is extended or adjusted under 35 U.S.C. 154(b) by 59 days.

(21) Appl. No.: 10/053,069

(22) Filed: Jan. 16, 2002

(65) Prior Publication Data

US 2003/0135139 A1 Jul. 17, 2003

(51) Int. Cl.[7] .......................... A61H 31/00; A61N 1/39
(52) U.S. Cl. ..................... 601/41; 607/3; 607/142
(58) Field of Search ................... 601/41, 44; 607/3, 607/5, 142, 145, 148, 149, 150

(56) References Cited

U.S. PATENT DOCUMENTS

| 4,060,079 A | | 11/1977 | Reinhold, Jr. |
|---|---|---|---|
| 4,570,615 A | | 2/1986 | Barkalow |
| 5,645,522 A | * | 7/1997 | Lurie et al. ................ 601/43 |
| 5,820,572 A | * | 10/1998 | Palmer .................... 601/41 |

OTHER PUBLICATIONS

2001–00471140 US patent Publication to Freeman Nov. 29, 2001.*

* cited by examiner

Primary Examiner—Danton D. DeMille
(74) Attorney, Agent, or Firm—McHale & Slavin, P.A.

(57) ABSTRACT

A medical cuirass or breastplate for use in CPR is made of a light weight rigid material in a shape to approximate a patient's chest area. The cuirass has defibrillator pads on the interior surface adapted to contact the chest. The defibrillator pads are in electrical contact with electrical connectors on the exterior surface. The electrical connectors are adapted to be connected to a defibrillator machine for electrical stimulation of the heart.

7 Claims, 1 Drawing Sheet

MEDICAL CUIRASS FOR CARDIO-PULMONARY RESUSCITATION

FIELD OF THE INVENTION

This invention relates to the emergency medical field of mechanical resuscitation involving direct compression of the chest cavity and stimulation of the heart.

BACKGROUND OF THE INVENTION

Cardio-pulmonary resuscitation, or CPR, is performed by external chest compression applied to the sternum area of a supine patient to massage the heart and cause forced pumping of blood from a temporarily stopped heart. A constant repetitive compression, followed by a short release of pressure, results in systolic and diastolic blood pressure in the patient. Proper CPR technique requires external pressure, either manually or mechanically, to force the sternum toward the spine while the patient's back is rigidly supported.

In addition to the compression strokes to the sternum, the patient must be ventilated to force oxygen rich air into the lungs. To accomplish this, the airway must be opened and air forced into the patient's mouth by another person or by a mechanical air pump device.

CPR has been taught to many people for use in emergency situations to sustain the patient until trained medical personnel take over treatment. The teaching standard is applying the heel of the hand to the patient's sternum and to avoid the patient's ribs. However, in the heat of the moment, the CPR has resulted in fractured ribs, sternum, and torn cartilage Further, since there are no standards set for mechanical CPR devices, the manufacturers have related the size of the mechanical piston which contacts the patient's sternum to the accepted size of the heel of the hand. Needless to say, the mechanical devices can, and do, apply as much, if not more, force to the patient's sternum. Therefore, while the mechanical devices may be more efficient in their operation, the problem of trauma to the sternum and ribs has not been directly addressed.

It is also well accepted medical practice to electrically stimulate a stopped heart or an arhythmatic heart to return to a normalized beat. This requires an electric shock to be delivered directly through the skin of the patient in the chest area by a defibrillator. If CPR is being performed, the personnel must be clear of the patient when the shock is delivered. If there is CPR equipment placed on or over the patient's chest, this must also be removed and CPR interrupted until the equipment is restored to proper position.

DESCRIPTION OF THE PRIOR ART

The Reinhold patent, U.S. Pat. No. 4,060,079 teaches the use of a portable mechanical CPR device which includes a compressed air operated cylinder/piston strapped on the chest, above the sternum, of a patient and a source of compressed breathable air.

Barkalow, U.S. Pat. No. 4,570,615, teaches the use of a compressible massager pad somewhat larger than the heel of the hand. The pad is filled with a gel and has structure for restricting lateral expansion of the pad.

What is needed in the art is a CPR device that will protect the ribs and sternum from localized trauma and provide the capability of electrical stimulation of the heart without a major interruption of the sequence of the CPR.

SUMMARY OF THE INVENTION

Accordingly, it is an objective of the instant invention to teach the use of a cuirass or breast plate which is strong enough to accept a manual or mechanical CPR stroke without local deformation.

It is a further objective of the instant invention to teach the use of a cuirass sized and shaped to cover the area of the chest defined by the diaphram and the armpits with lateral curvature over the ribs.

It is yet another objective of the instant invention to teach the provision of defibrillator pads on the interior surface of the cuirass for applying electrical stimulation to the heart.

It is a still further objective of the invention teach the provision of electrical leads from the defibrillator pads through the cuirass integrated into electrical connectors on the external surface of the cuirass.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
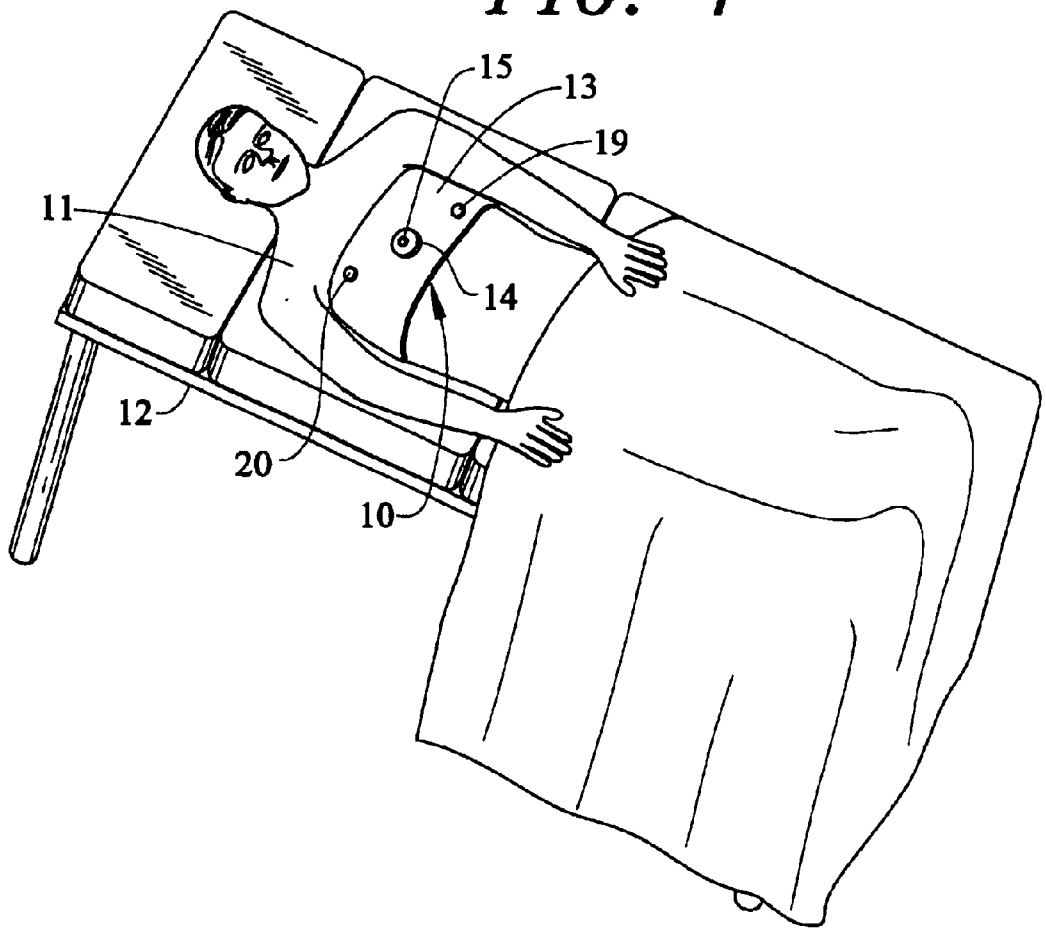
FIG. 1 shows a perspective of the cuirass of this invention applied to a patient.
Figure 2:
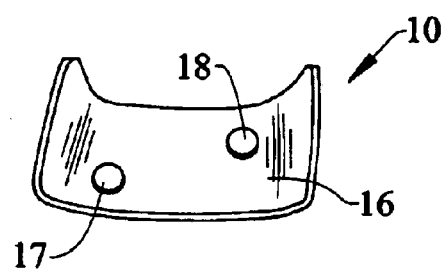
FIG. 2 shows a perspective of the interior of the cuirass with the defibrillation pads in place.

The cuirass 10, as shown in FIG. 1, may be of any light weight material, including metals and hard polymers, that may be molded or shaped as a shell to approximate the chest area of a patient 11. The patient 11 is lying on a table 12 or other hard surface for rigid support of the chest cavity and spine.

The cuirass 10 has sufficient thickness and/or rigidity to withstand a blow, of substantially greater force than required for CPR, without localized deformation. This strength distributes the force throughout the surface of the cuirass and protects the sternum and ribs from damage. As a result of the blow, the volume of the entire chest cavity is reduced to force blood from the heart.

The outer surface 13 of the cuirass 10 may have markings 14 to designate the proper area over the heart for application of manual or mechanical compression strokes. These markings 14 would also serve as a guide for the proper placement of the cuirass 10 upon different sized patients. Of course, if there are large variations in size of patients, the cuirass may be made in different sizes to accommodate adults, children, men and women.

The exterior surface 13 may have a depression or/and roughened area 15 about the markings 14 to improve the purchase between the cuirass 10 and the hands or mechanical device applying compression to the patient.

The interior surface 16 is in intimate contact with the patient. This surface 16 acts as a piston to depress the chest and reduce the volume of the chest cavity in response to the CPR stroke. Embedded in the cuirass 10 are two defibrillator pads 17 and 18. The interior surface of each pad is exposed on the interior surface 16 and contacts the patient. The pads 17 and 18 may be permanently fixed in the cuirass or they may be removable or the cuirass may be made without the pads.

Each pad, 17 and 18, has an electrical lead (not shown) that extends through the cuirass 10 to the exterior surface 13. Each lead is connected to an electrical connector mounted on the exterior surface. Electrical connectors 19 and 20 are adapted for connecting the pads 17 and 18, respectively, to a defibrillator machine OR intermediary unit. The electrical connectors may be directly connected, by cables, or may have quick-connect or plug-in structure. During the CPR procedure, it may be desirable to perform a defibrillation to start a stopped heart or to regulate an erratic heart beat. The electrical shock may be given with the cuirass 10 in place and, if necessary, CPR may be continued immediately.

If the cuirass 10 is made of a metal, the pads 17 and 18 with the associated leads and the connectors 19 and 20 would be adequately insulated from the metal.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A medical cuirass for protecting a patient undergoing CPR comprising a shell adapted to cover the chest area, said shell having an interior surface for contacting the patient and an exterior surface for receiving the compression stroke of CPR, said shell being of sufficient stiffness to translate a CPR compression stroke evenly throughout said interior surface whereby the patient is not subject to localized trauma wherein said exterior surface has a marking adapted to guide the placement of the cuirass upon a patient, said marking including a roughened area providing improved purchase on said cuirass.

2. A medical cuirass of claim 1 wherein said shell is made of a material which is non-conductive to electricity.

3. A medical cuirass of claim 1 wherein an electric lead extends through said shell to said exterior surface, electrical connectors on said exterior surface adapted for connection to a defibrillator machine.

4. A medical cuirass of claim 1 wherein said shell is made of metal.

5. A medical cuirass of claim 4 wherein said interior surface carries defibrillator pads, said pads having electrical leads extending through said shell to electrical connectors on said exterior surface, said pads, said leads and said connectors insulated from said metal shell.

6. A medical cuirass for protecting the ribs and sternum of a patient undergoing CPR comprising a lightweight rigid shell having a surface area adapted to approximate the chest area of a patient, said shell having an interior surface and an exterior surface, said shell being of sufficient stiffness to translate a CPR compression stroke evenly throughout said interior surface, said interior surface adapted to contact the chest area of a patient, said interior surface including defibrillator pads, electrical connectors on said exterior surface, said pads electrically connected to said electrical connectors, said electrical connectors adapted to be connected to a defibrillator machine wherein said pads are removable and said electrical connectors including means for electrical connection to a defribillator.

7. A medical cuirass of claim 6 wherein said pads are permanently fixed in said interior surface and said electrical connectors including means for electrical connection to a defribillator.

* * * * *